(12) United States Patent
Banas et al.

(10) Patent No.: US 8,313,523 B2
(45) Date of Patent: Nov. 20, 2012

(54) METALLIC IMPLANTABLE GRAFTS AND METHOD OF MAKING SAME

(75) Inventors: Christopher E. Banas, San Antonio, TX (US); Julio C. Palmaz, San Antonio, TX (US)

(73) Assignee: Advanced Bio Prosthetic Surfaces, Ltd., Dallas, TX (US)

( * ) Notice: Subject to any disclaimer, the term of this patent is extended or adjusted under 35 U.S.C. 154(b) by 0 days.

(21) Appl. No.: 10/840,205

(22) Filed: May 6, 2004

(65) Prior Publication Data

US 2005/0033418 A1    Feb. 10, 2005

Related U.S. Application Data

(60) Provisional application No. 60/468,425, filed on May 7, 2003.

(51) Int. Cl.
*A61F 2/06* (2006.01)

(52) U.S. Cl. ............... 623/1.28; 623/1.39; 623/1.49

(58) Field of Classification Search ........ 623/1.11–1.54, 623/23.64–23.71
See application file for complete search history.

(56) References Cited

U.S. PATENT DOCUMENTS

| | | | |
|---|---|---|---|
| 3,945,052 A | 3/1976 | Liebig | 3/1 |
| 4,510,182 A | 4/1985 | Cornils et al. | 427/162 |
| 4,517,687 A | 5/1985 | Liebig et al. | 3/1.4 |
| 4,733,665 A | 3/1988 | Palmaz | 604/104 |
| 4,739,762 A | 4/1988 | Palmaz | 604/104 |
| 4,751,099 A | 6/1988 | Niino et al. | 427/34 |
| 4,776,337 A | 10/1988 | Palmaz | 623/1 |
| 4,846,834 A | 7/1989 | von Recum et al. | 623/66 |
| 5,049,251 A | 9/1991 | Inoue | 204/192 |
| 5,061,914 A | 10/1991 | Busch et al. | 337/140 |
| 5,084,151 A | 1/1992 | Vallana et al. | 204/192.11 |
| 5,102,417 A | 4/1992 | Palmaz | 604/8 |
| 5,133,845 A | 7/1992 | Vallana et al. | 204/192 |
| 5,158,750 A | 10/1992 | Finicle | 422/102 |

(Continued)

FOREIGN PATENT DOCUMENTS

DE      1452370      3/1974

(Continued)

OTHER PUBLICATIONS

Multilayer Ceramic/Metallic Coatings by Ion Beam-Assisted, Electron Beam Physical Vapor (EB-PVD) Deposition, Penn State Applied Research Laboratory, pp. 1-4 (1997).

(Continued)

*Primary Examiner* — David Isabella
*Assistant Examiner* — Suba Ganesan
(74) *Attorney, Agent, or Firm* — J. Peter Paredes; Rosenbaum & Silvert, P.C.

(57) ABSTRACT

Implantable medical grafts fabricated of metallic or pseudometallic films of biocompatible materials having a plurality of microperforations passing through the film in a pattern that imparts fabric-like qualities to the graft or permits the geometric deformation of the graft. The implantable graft is preferably fabricated by vacuum deposition of metallic and/or pseudometallic materials into either single or multi-layered structures with the plurality of microperforations either being formed during deposition or after deposition by selective removal of sections of the deposited film. The implantable medical grafts are suitable for use as endoluminal or surgical grafts and may be used as vascular grafts, stent-grafts, skin grafts, shunts, bone grafts, surgical patches, non-vascular conduits, valvular leaflets, filters, occlusion membranes, artificial sphincters, tendons and ligaments.

15 Claims, 9 Drawing Sheets

U.S. PATENT DOCUMENTS

| | | | |
|---|---|---|---|
| 5,242,710 A | 9/1993 | Claar et al. | 427/248 |
| 5,277,933 A | 1/1994 | Claar et al. | 427/248 |
| 5,370,684 A | 12/1994 | Vallana et al. | 623/1 |
| 5,383,927 A * | 1/1995 | De Goicoechea et al. | 623/1.43 |
| 5,387,247 A | 2/1995 | Vallana et al. | 623/2 |
| 5,421,955 A | 6/1995 | Lau et al. | 216/48 |
| 5,423,885 A | 6/1995 | Williams | 623/1 |
| 5,540,820 A | 7/1996 | Terakado et al. | 204/192.3 |
| 5,545,210 A | 8/1996 | Hess et al. | 623/1 |
| 5,569,272 A | 10/1996 | Reed et al. | 606/151 |
| 5,593,442 A | 1/1997 | Klein | 623/12 |
| 5,605,714 A | 2/1997 | Dearnaley et al. | 427/2.24 |
| 5,607,463 A | 3/1997 | Schwartz et al. | 623/1 |
| 5,609,629 A | 3/1997 | Fearnot et al. | 623/1 |
| 5,647,858 A | 7/1997 | Davidson | 604/264 |
| 5,683,453 A | 11/1997 | Palmaz | 623/1 |
| 5,685,961 A | 11/1997 | Pourrezaei et al. | 204/192 |
| 5,690,670 A | 11/1997 | Davidson | 606/198 |
| 5,723,219 A | 3/1998 | Kolluri et al. | 428/411.1 |
| 5,725,556 A * | 3/1998 | Moser et al. | 606/232 |
| 5,725,573 A | 3/1998 | Dearnaley et al. | 623/2 |
| 5,728,150 A | 3/1998 | McDonald et al. | 623/1 |
| 5,735,892 A | 4/1998 | Myers et al. | 623/1 |
| 5,735,896 A | 4/1998 | Amon et al. | 623/11 |
| 5,749,880 A * | 5/1998 | Banas et al. | 606/198 |
| 5,765,418 A | 6/1998 | Rosenberg | 72/47 |
| 5,772,864 A | 6/1998 | Moller et al. | 205/73 |
| 5,782,908 A | 7/1998 | Cahalna et al. | 623/1 |
| 5,782,910 A | 7/1998 | Davidson | 623/3 |
| 5,824,045 A | 10/1998 | Alt | 623/1 |
| 5,824,056 A | 10/1998 | Rosenberg | 623/606 |
| 5,843,120 A | 12/1998 | Israel et al. | 606/198 |
| 5,843,289 A | 12/1998 | Lee et al. | 204/192 |
| 5,849,206 A | 12/1998 | Amon et al. | 216/37 |
| 5,855,802 A | 1/1999 | Acciai et al. | 216/8 |
| 5,855,955 A | 1/1999 | Claar et al. | 427/248.1 |
| 5,858,556 A | 1/1999 | Eckert et al. | 428/586 |
| 5,873,904 A | 2/1999 | Ragheb et al. | 623/1 |
| 5,895,419 A | 4/1999 | Tweden et al. | 623/2 |
| 5,902,332 A | 5/1999 | Schatz | 623/1 |
| 5,928,279 A | 7/1999 | Shannon et al. | 623/1 |
| 5,932,299 A | 8/1999 | Katoot | 427/508 |
| 5,945,153 A | 8/1999 | Dearnaley | 427/2.12 |
| 5,951,881 A | 9/1999 | Rogers et al. | 216/41 |
| 5,962,138 A | 10/1999 | Kolluri et al. | 428/411.1 |
| 5,972,018 A | 10/1999 | Israel et al. | 606/198 |
| 5,984,905 A | 11/1999 | Dearnaley | 604/265 |
| 6,013,054 A | 1/2000 | Jiun Yan | 604/96 |
| 6,039,755 A | 3/2000 | Edwin et al. | 623/1 |
| 6,096,175 A | 8/2000 | Roth | 204/192 |
| 6,103,320 A | 8/2000 | Matsumoto et al. | 427/535 |
| 6,113,750 A | 9/2000 | Shinmura et al. | 204/192.15 |
| 6,120,536 A | 9/2000 | Ding et al. | 623/11.43 |
| 6,124,523 A | 9/2000 | Banas et al. | 623/1 |
| 6,193,745 B1 | 2/2001 | Fogarty et al. | 623/1.12 |
| 6,197,013 B1 | 3/2001 | Reed et al. | 604/509 |
| 6,207,536 B1 | 3/2001 | Matsumoto et al. | 438/478 |
| 6,264,684 B1 | 7/2001 | Banas et al. | 623/1.13 |
| 6,264,687 B1 | 7/2001 | Tomonto | 623/1.16 |
| 6,274,014 B1 | 8/2001 | Matsumoto et al. | |
| 6,287,277 B1 | 9/2001 | Yan | 604/96.01 |
| 6,287,335 B1 * | 9/2001 | Drasler et al. | 623/1.28 |
| 6,287,435 B1 | 9/2001 | Drewery et al. | 204/298.09 |
| 6,290,721 B1 | 9/2001 | Heath | 623/1.15 |
| 6,293,967 B1 | 9/2001 | Shanley | 623/1.15 |
| 6,312,463 B1 | 11/2001 | Rourke et al. | 623/1.39 |
| 6,325,825 B1 * | 12/2001 | Kula et al. | 623/1.3 |
| 6,331,191 B1 | 12/2001 | Chobotov | 623/1.44 |
| 6,358,275 B1 | 3/2002 | Mcllroy et al. | 623/1.28 |
| 6,383,214 B1 | 5/2002 | Banas et al. | 623/1.14 |
| 6,451,047 B2 | 9/2002 | McCrea et al. | 623/1.13 |
| 6,458,152 B1 | 10/2002 | Khosravi et al. | 623/1.13 |
| 6,974,471 B2 * | 12/2005 | Van Schie et al. | 623/1.12 |
| 2001/0021870 A1 | 9/2001 | Edwin et al. | 623/1.19 |
| 2001/0032013 A1 | 10/2001 | Marton | |
| 2001/0039449 A1 | 11/2001 | Johnson et al. | 623/1.19 |
| 2002/0156522 A1 | 10/2002 | Ivancev et al. | 623/1.13 |
| 2003/0004567 A1 | 1/2003 | Boyle et al. | 623/195 |
| 2003/0028246 A1 | 2/2003 | Palmaz et al. | 623/1.13 |
| 2003/0176912 A1 * | 9/2003 | Chuter et al. | 623/1.13 |
| 2004/0019375 A1 * | 1/2004 | Casey et al. | 623/1.28 |

FOREIGN PATENT DOCUMENTS

| | | |
|---|---|---|
| EP | 0 400 947 | 5/1990 |
| EP | 0 442 303 | 1/1991 |
| JP | 51055724 | 5/1976 |
| JP | 11267462 | 10/1999 |
| WO | WO 92/19310 * | 11/1992 |
| WO | 97/07257 | 2/1997 |
| WO | 97/44692 | 11/1997 |
| WO | 99/23977 | 5/1999 |
| WO | 99/62432 | 12/1999 |
| WO | 00/04204 | 1/2000 |
| WO | 00/54704 | 9/2000 |
| WO | 01/21851 | 3/2001 |
| WO | 01/21852 | 3/2001 |
| WO | 01/43790 | 6/2001 |
| WO | 01/53559 | 7/2001 |
| WO | 01/55473 | 8/2001 |
| WO | 01/56502 | 8/2001 |
| WO | WO 01/74274 A2 * | 10/2001 |

OTHER PUBLICATIONS

"The Effects of Ion Irradiation on NiTi Shape Memory Alloy Thin Films" by F. Goldberg and E. Knystautas, *Proceedings of the Second International Conference on Shape Memory and Superelastic Technologies Asilomar Conference Center*, Pacific Grove, California, USA, pp. 177-182 (1997).

"Vacuum Conditions for Sputtering Thin Film TiNi", *Journal of Vacuum Science and Technology, JVST A Online*, pp. 1-2 (Abstract view).

"Relative importance of bombardment energy and intensity in ion plating", K.S. Fancey, et al., *Journal of Vacuum Science & Technology A: Vacuum, Surfaces and Films*, vol. 13, Issue 2, pp. 428-435 (Abstract view) Mar. 1995.

"Thin Film Shape Memory Microvalves with Adjustable Operation Temperature" by Kohl, Dittmann, Quandt and Winzek, *Sensors and Actuators*, vol. 83, pp. 214-219, (2000).

"Multicomponent Film Deposition by Target Biasing", *IBM Technical Disclosure Bulletin*, pp. 1-2 (Jul. 1980).

"Oriented nickel-titanium shape memory alloy films prepared by annealing during deposition" by Kathleen Gisser, et al., *Applied Physics Letters*, vol. 61, Issue 14, pp. 1632-1634 (Abstract View).

"Thin Film Shape Memory Alloy Microactuators" by TiNI Alloy Company (online).

"A Concise History of Vacuum Coating Technology, Part 2:1940 to 1975" by D. Mattox, www.svc.org/HistoryofVac2.htm, pp. 1-15.

"Constitutive Parts of a Shape Memory Alloy Titanium Nickel Thin Film Catheter" by L. Buchaillot, et al., *Proceedings of the Second International Conference on Shape Memory and Superelastic Technologies Asilomar Conference Center*, Pacific Gove, California, USA, pp. 183-188 (1997).

"The Characteristics of NiTi HCDd-Deposited SMA Films" by H. Weixin, et al., *Proceedings of the Second International Conference on Shape Memory and Superelastic Technologies Asilomar Conference Center*, Pacific Gove, California, USA, pp. 167-172 (1997).

"Microstructure of Ti-Rich TiNi Thin Films" by A. Ishida, et al., *Proceedings of the Second International Conference on Shape Memory and Superelastic Technologies Asilomar Conference Center*, Pacific Gove, California, USA, pp. 161-166 (1997).

"The Experimental Use of Steel Mesh Tubes for the Replacement of Arterial Segments," by Larry, Banning G., M.D., et al., *Presented at the Third Scientific Meeting of the North American Chapter of the International Society of Angiology*, Atlantic City, NJ, pp. 69-75 (Jun. 4, 1955).

"Progress in Thin Film Shape Memory Microactuators," by Johnson, et al., www.sma-mems.com/recent.htm (Overview), pp. 105.

"A Concise History of Vacuum Coating Technology, Part 2: 1940 to 1975," by D. Mattox, www.svc.org/HistoryofVac2.html, pp. 1-5.

"Model Surfaces for Studying and Controlling the Adhesion of Cells" by M. Mrksich, AVS 47th International Symposium, Invited Paper No. BI+EL-TuA1 (Oct. 3, 2000).

"Cell Response to Chemically and Topographically Modified Surfaces" by D.S. Sutherland, et al., AVS 47th International Symposium, Invited Paper No. BI+EL-TuA3 (Oct. 3, 2000).

"Tissue Formation of Hepatocytes on Micro-Porous Films of Polylactide" by T. Nishikawa, et al, AVS 47th International Symposium, Invited Paper No. BI+EL-TuA10 (Oct. 3, 2000).

"Endothelial Cell Organization on Micropatterned Protein Surfaces" by R. Daw, et al., AVS 47th International Symposium, Invited Paper No. BI-WeP21 (Oct. 4, 2000).

"The Nanomechanical Properties of Thin Films" by J.E. Houston, AVS 47th International Symposium, Invited Paper No. TF-TuA1 (Oct. 3, 2000).

"Porous and nonporous polycarbonate Urethane stent-grafts for TIPS formation: biologic responses (abstract)" by Z.J. Haskal and L.J. Brennecke, *J. Vasc. Interv. Radiol*, vol. 10, No. 9, pp. 1255-1263 (Oct. 1999).

"Primary Implantation of Polyester-Covered Stent-Grafts for Transjugluar Introhepatic Portosystemic Stent Shunts (TiPSS): A Pilot Study" by Manfred Cejna, et al., *Cardiovasc Intervent Radiol*, vol. 22, pp. 305-310 (1999).

"Sputtering Targets High-Quality Thin Film Materials" by AMETEK Specialty Metal Products online at www.ametek84.com/fd-sputtering.html, pp. 1-3.

"The influence of Ion Irradiation during film growth on the chemical stability of film/substrate systems" by W. Ensinger, *Surface and Coatings Technology*, vol. 80, pp. 35-48 (1996).

"Anomalous Plastic and Elastic Behaviors of Sputter-deposited TiN with 10 or 20 Inserted Thin Al Layers Evaluated by Nanoindentatlon" by E. Kusano, et al., AVS 47th International Symposium, Paper No. TF-TuA3 (Oct. 3, 2000).

"Recent Progress in the Application of Thin Film Shape Memory Alloys" by A.D. Johnson and J.D. Busch, *Proceedings of the First International Conference on Shape Memory and Superelastic Technologies Asilomar Conference Center*, Pacific Grove, California, USA, pp. 299-310 (1994).

"Shape Memory Properties in NiTI Sputter-deposited Film", by J.D. Busch and A.D. Johnson, *J Appl. Phys*, vol. 68, No. 12, pp.6224-6226 (Dec. 15, 1990).

"Thin-film Processing of TiNi Shape Memory Alloy" by J.A. Waker and K.J. Gabriel, *Sensors and Actuators*, A21-A23, pp. 243-246 (1990).

"Sputter-deposition of TiNi, TiNiPd and TiPd films displaying the two-way shape-memory effect" by E. Quandt, et al., *Sensors and Actuators*, A 53, pp. 434-439 (1996).

"Applications of Shape-Memory Alloy Thin Films" by A.D. Johnson and V.V. Martynov, *Proceedings of the Second International Conference on Shape Memory and Superelastic Technologies Asilomar Conference Center*, Pacific Grove, California, USA, pp. 1-8 (1997).

"Liquid Sources for Chemical Vapor Deposition of Group 6 Metals and Metal Nitrides" by Gordon, et al., www.techtransfer.harvard.edu/cgi-bln/TALSearch.cgi?full_report=1&case=3, Case No. 1709.

"Stents: Literature," http://www.phytis.com/liter.htm, pp. 1-8.

Supplementary European Search Report, pp. 1-4, (Jan. 29, 2008).

\* cited by examiner

METALLIC IMPLANTABLE GRAFTS AND METHOD OF MAKING SAME

CROSS REFERENCE TO RELATED APPLICATIONS

The present application claims priority to provisional application, U.S. Ser. No. 60/468,425, filed May 7, 2003, and is related to commonly assigned, co-pending U.S. applications Ser. Nos. 10/135,136 filed Apr. 29, 2002, now U.S. Pat. No. 7,300,457, which claims priority from U.S. Ser. No. 60/310,617, filed Aug. 7, 2001, U.S. Ser. No. 09/745,304, filed Dec. 22, 2000, now U.S. Pat. No. 6,820,676, which is a divisional of Ser. No. 09/443,929, filed Nov. 19, 1999, now U.S. Pat. No. 6,379,383, and U.S. Ser. Nos. 10/289,974 and 10/289,843 both filed Nov. 6, 2002, now U.S. Pat. Nos. 7,491,226 and 7,641,680, which are continuation applications of U.S. Ser. No. 09/532,164, filed Mar. 20, 2000, now U.S. Pat. No. 6,537,310.

BACKGROUND OF THE INVENTION

The present invention relates generally to implantable metallic medical devices. More specifically, the present invention relates to implantable medical devices, including, for example, surgical and endoluminal vascular grafts, stent grafts, covered stents, skin grafts, shunts, bone grafts, surgical patches, non-vascular conduits, valvular leaflets, filters, occlusion membranes, sphincters, artificial tendons and ligaments. More specifically, the present invention relates to implantable medical grafts fabricated of metallic or pseudometallic films of biocompatible materials and having a plurality of pleats or corrugations in the film. Where the graft is of a generally tubular shape, the pleats or corrugations are preferably circumferential and axially positioned along the longitudinal axis of the graft. In accordance with a preferred embodiment of the invention, the inventive medical grafts may have a plurality of microperforations passing through the film. The plurality of microperforations may serve multiple purposes, including, for example, permitting geometric deformation of the film, imparting a fabric-like quality to the film, imparting flexibility to the film, permitting tissue ingrowth and promoting healing. The term "fabric-like" is intended to mean a quality of being pliable and/or compliant in a manner similar to that found with natural or synthetic woven fabrics. The inventive medical grafts may have both perforated and imperforated regions along at least portions of the surface area of the graft.

The inventive implantable grafts are fabricated entirely of self-supporting, coherent films made of biocompatible metals or biocompatible pseudometals. Heretofore in the field of implantable medical devices, it is unknown to fabricate an implantable medical device that comprises a graft as at least as one of its elements, such as a stent graft or covered stent, fabricated entirely of self-supporting, coherent metal or pseudometal materials. As used herein the term "graft" is intended to indicate any type of device or part of a device that comprises essentially a material delimited by two surfaces where the distance between said surfaces is the thickness of the graft and exhibits integral dimensional strength to be self-supporting such that it is capable of use in vivo without the need for an ancillary supporting structure, such as a stent or other structural reinforcement to maintain an enlarged in vivo diameter. The inventive graft may have microperforations that pass through regions of the thickness of the graft such that the graft has imperforate regions and microperforate regions, or may have microperforations through all wall surfaces of the graft or be completely imperforate. The inventive grafts may be formed in planar sheets, toroids, and in other shapes as particular applications may warrant. However, for purposes of illustration only, the present application will refer to tubular grafts. For purposes of this application, the terms "pseudometal" and "pseudometallic" are intended to mean a biocompatible material which exhibits biological response and material characteristics substantially the same as biocompatible metals. Examples of pseudometallic materials include, for example, composite materials and ceramics. Composite materials are composed of a matrix material reinforced with any of a variety of fibers made from ceramics, metals, carbon, or polymers.

When implanted into the body, metals are generally considered to have superior biocompatibility than that exhibited by polymers used to fabricate commercially available polymeric grafts. It has been found that when prosthetic materials are implanted, integrin receptors on cell surfaces interact with the prosthetic surface. The integrin receptors are specific for certain ligands in vivo. If a specific protein is adsorbed on a prosthetic surface and the ligand exposed, cellular binding to the prosthetic surface may occur by integrin-ligand docking. It has also been observed that proteins bind to metals in a more permanent fashion than they do to polymers, thereby providing a more stable adhesive surface. The conformation of proteins coupled to surfaces of most medical metals and alloys appears to expose greater numbers of ligands and preferentially attract endothelial cells having surface integrin clusters to the metal or alloy surface relative to leukocytes. Finally, metals and metal alloys exhibit greater resistance to degradation of metals relative to polymers, thereby providing greater long-term structural integrity and stable interface conditions.

Because of their relatively greater adhesive surface profiles, metals are also susceptible to short-term platelet activity and/or thrombogenicity. These deleterious properties may be offset by administration of pharmacologically active antithrombogenic agents in routine use today. Surface thrombogenicity usually disappears 1-3 weeks after initial exposure. Antithrombotic coverage is routinely provided during this period of time for coronary stenting. In non-vascular applications such as musculoskeletal and dental, metals have also greater tissue compatibility than polymers because of similar molecular considerations. The best article to demonstrate the fact that all polymers are inferior to metals is van der Giessen, W. J. et al. Marked inflammatory sequelae to implantation of biodegradable and non-biodegradable polymers in porcine coronary arteries, *Circulation,* 1996:94(7):1690-7.

Normally, endothelial cells (EC) migrate and proliferate to cover denuded areas until confluence is achieved. Migration, quantitatively more important than proliferation, proceeds under normal blood flow roughly at a rate of 25 µm/hr or 2.5 times the diameter of an EC, which is nominally 10 µm. EC migrate by a rolling motion of the cell membrane, coordinated by a complex system of intracellular filaments attached to clusters of cell membrane integrin receptors, specifically focal contact points. The integrins within the focal contact sites are expressed according to complex signaling mechanisms and eventually couple to specific amino acid sequences in substrate adhesion molecules. An EC has roughly 16-22% of its cell surface represented by integrin clusters. Davies, P. F., Robotewskyi A., Griem M. L. Endothelial cell adhesion in real time. *J. Clin. Invest.* 1993; 91:2640-2652, Davies, P. F., Robotewski, A., Griem, M. L., Qualitative studies of endothelial cell adhesion, *J. Clin. Invest.* 1994; 93:2031-2038. This is a dynamic process, which implies more than 50% remodeling in 30 minutes. The focal adhesion contacts vary in size and distribution, but 80% of them measure less than 6 μm², with the majority of them being about 1 μm², and tend to elongate in the direction of flow and concentrate at leading edges of the cell. Although the process of recognition and signaling to determine specific attachment receptor response to attachment sites is incompletely understood, availability of attachment sites will favorably influence attachment and migration. It is known that materials commonly used as medical grafts, such as polymers, do not become covered with EC and therefore do not heal after they are placed in the arteries. It is therefore an object of this invention to replace polymer grafts with metal grafts that can potentially become covered with EC and can heal completely. Furthermore, heterogeneities of materials in contact with blood flow may be controlled by using vacuum deposition techniques to form the materials to make the inventive grafts.

There have been numerous attempts to increase endothelialization of implanted medical devices such as stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649,951), coating a stent with a layer of turbostatic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene, (U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299). However, these approaches fail to remedy the lack of clinically acceptable endothelialization of polymer grafts.

It is, therefore, desirable that the inventive graft be fabricated entirely of metallic and/or pseudometallic materials wherein at least a portion of the wall surfaces of the graft have a plurality of pleats or undulations to provide a self-supporting, stand-alone graft that exhibits a greater capacity for endothelialization than that of conventional polymeric grafts.

The inventive metal devices are preferably fabricated by thin film vacuum deposition techniques such as sputtering or physical vapor deposition processes. In accordance with the present invention, it is preferable to fabricate the inventive implantable devices by vacuum deposition. Vacuum deposition permits greater control over many material characteristics and properties of the resulting formed device. For example, vacuum deposition permits control over grain size, grain phase, grain material composition, bulk material composition, surface topography, mechanical properties, such as transition temperatures in the case of a shape memory alloy. Moreover, vacuum deposition processes permit creation of devices with greater material purity without the introduction of large quantities of contaminants that adversely affect the material, mechanical or biological properties of the implanted device. Vacuum deposition techniques also lend themselves to fabrication of more complex devices than those susceptible of manufacture by conventional cold-working techniques. For example, multi-layer structures, complex geometrical configurations, extremely fine control over material tolerances, such as thickness or surface uniformity, are all advantages of vacuum deposition processing.

In vacuum deposition technologies, materials are formed directly in the desired geometry, e.g., planar, tubular, etc. and have a pre-determined surface topography based upon the surface topography of a deposition substrate onto which a metal or pseudometal is deposited, conforming to the substrate topography. The common principle of vacuum deposition processes is to take a material in a minimally processed form, such as pellets or thick foils, known as the source material and atomize them. Atomization may be carried out using heat, as is the case in physical vapor deposition, or using the effect of collisional processes, as in the case of sputter deposition, for example. In some forms of deposition, a process, such as laser ablation, which creates microparticles that typically consist of one or more atoms, may replace atomization; the number of atoms per particle may be in the thousands or more. The atoms or particles of the source material are then deposited on a substrate or mandrel to directly form the desired object. In other deposition methodologies, chemical reactions between ambient gas introduced into the vacuum chamber, i.e., the gas source, and the deposited atoms and/or particles are part of the deposition process. The deposited material includes compound species that are formed due to the reaction of the solid source and the gas source, such as in the case of chemical vapor deposition. In most cases, the deposited material is then either partially or completely removed from the substrate, to form the desired product.

A first advantage of vacuum deposition processing is that vacuum deposition of the metallic and/or pseudometallic films permits tight process control and films may be deposited that have regular, homogeneous atomic and molecular pattern of distribution along their fluid-contacting surfaces. This avoids the marked variations in surface composition, creating predictable oxidation and organic adsorption patterns and has predictable interactions with water, electrolytes, proteins and cells. Particularly, EC migration is supported by a homogeneous distribution of binding domains that serve as natural or implanted cell attachment sites, in order to promote unimpeded migration and attachment.

Secondly, in addition to materials and devices that are made of a single metal or metal alloy, henceforth termed a layer, the inventive grafts may be comprised of a layer of biocompatible material or of a plurality of layers of biocompatible materials formed upon one another into a self-supporting multilayer structure. Multilayer structures are generally known to increase the mechanical strength of sheet materials, or to provide special qualities by including layers that have special properties such as superelasticity, shape memory, radio-opacity, corrosion resistance etc. A special advantage of vacuum deposition technologies is that it is possible to deposit layered materials and thus films possessing exceptional qualities may be produced (cf., H. Holleck, V. Schier: Multilayer PVD coatings for wear protection, *Surface and Coatings Technology*, Vol. 76-7 (1995) pp. 328-336). Layered materials, such as superstructures or multilayers, are commonly deposited to take advantage of some chemical, electronic, or optical property of the material as a coating; a common example is an antireflective coating on an optical lens. Multilayers are also used in the field of thin film fabrication to increase the mechanical properties of the thin film, specifically hardness and toughness.

Thirdly, the design possibilities for possible configurations and applications of the inventive graft are greatly enhanced by employing vacuum deposition technologies. Specifically, vacuum deposition is an additive technique that lends itself toward fabrication of substantially uniformly thin materials with potentially complex three dimensional geometries and structures that cannot be cost-effectively achieved, or in some cases achieved at all, by employing conventional wrought fabrication techniques. Conventional wrought metal fabrication techniques may entail smelting, hot working, cold working, heat treatment, high temperature annealing, precipitation annealing, grinding, ablation, wet etching, dry etching, cutting and welding. All of these processing steps have disadvantages including contamination, material property degradation, ultimate achievable configurations, dimensions and tolerances, biocompatibility and cost. For example conventional wrought processes are not suitable for fabricating tubes having diameters greater than about 20 mm diameter, nor are such processes suitable for fabricating materials having wall thicknesses down to about 5 µm with sub-µm tolerances.

While the inventive self-supporting metal or pseudometal graft may be fabricated of conventionally fabricated wrought materials, in accordance with the best mode contemplated for the present invention, the inventive graft is preferably fabricated by vacuum deposition techniques. By vacuum depositing the metal and/or pseudometallic film as the precursor material for the inventive graft, it is possible to more stringently control the material, biocompatibility and mechanical properties of the resulting film material and graft than is possible with conventionally fabricated graft-forming materials. The inventive self-supporting graft may be used alone, i.e., the whole implantable device may be made of a single graft, or it may be a part of a structure where the graft is used in conjunction either with other grafts, or in conjunction with other structural elements, such as scaffolds, stents, and other devices. The term "in conjunction" may mean actual connection, such as that made by welding, fusing, or other joining methods, as well as being made from the same piece of material by forming some area of the piece into a graft and some other area of the piece into another member or part of the device.

SUMMARY OF THE INVENTION

In accordance with a preferred embodiment of the invention, there is provided a self-supporting graft member having a plurality of pleats or corrugations in wall surfaces thereof and may have a plurality of microperforations passing through the wall thickness of the graft. While the inventive graft member may assume virtually any geometric configuration, including sheets, tubes or rings, preferred geometries for the graft member are generally planar and generally tubular. Where present, the plurality of microperforations serve to impart geometric compliance to the graft, geometric distendability to the graft and/or limit or permit the passage of body fluids or biological matter through the graft, such as facilitating transmural endothelialization while preventing fluid flow through the wall of the graft under normal physiological conditions. The plurality of microperforations may also impart a fabric-like quality to the graft by imparting pliability and/or elastic, plastic or superelastic compliance to the graft, such as that required for longitudinal flexibility in the case of a vascular graft.

In a first embodiment, the graft may be made from plastically deformable materials such that upon application of a force, the microperforations geometrically deform to impart permanent enlargement of one or more axes of the graft, such as length in the case of a planar graft, e.g., a surgical patch graft, or diameter, such as in the case of a tubular graft, e.g., a vascular graft. In a second embodiment, the graft may be fabricated of elastic or superelastic materials. Elastic and/or superelastic materials will permit the microperforations to geometrically deform under an applied force in a manner that allows for a recoverable change in one or more axes of the graft.

In each of the first and second embodiments of the invention, the graft may be fabricated in such a manner as to have fabric-like qualities by controlling the film thickness, material properties and geometry of the plurality of microperforations. Furthermore, in such cases where minimally invasive delivery is required, such as for endoluminal delivery of vascular grafts, the first and second embodiments allow for delivery using balloon expansion and self-expansion, respectively, or a combination of both. Minimally invasive delivery may also be accomplished by folding the graft for delivery similar to the manner in which an angioplasty balloon is creased and fluted or folded. The graft may be delivered by unfolding the device in vivo either by assistance such as by using a balloon, or by the graft material's plastic, elastic or superelastic properties or by a combination thereof. After delivery, the plurality of microperforations may be patterned in such a manner as to allow for additional dimensional enlargement of the graft member by elastic or plastic deformation such as a radially expansive positive pressure.

The inventive metallic or pseudometallic graft may be employed as a surgically implanted graft, such as, for bypass grafting applications that require access by surgical procedures and suturing the graft to an existing anatomical structure. The inventive graft is highly suturable and exhibits suture retention strengths comparable to conventional synthetic polymeric grafts such as those fabricated from expanded polytetrafluoroethylene or polyester.

For some applications it is preferable that the size of each of the plurality of microperforations be such as to permit cellular migration through each opening, without permitting fluid flow there through. In this manner, for example, blood cannot flow through the plurality of microperforations, in either their deformed or un-deformed state, but various cells or proteins may freely pass through the plurality of microperforations to promote graft healing in vivo. For other applications, moderate amounts of fluid flow through the plurality of deformed or un-deformed microperforations may be acceptable. For example, endoluminal saphenous vein grafts may be fabricated with microperforations that serve the dual function of permitting transmural endothelialization while also excluding biological debris, such as thrombus from passing through the wall thickness of the graft, effectively excluding detrimental matter from entering the circulation. In this example, each of the plurality of microperforations in either their deformed or undeformed state, may exceed several hundred microns.

Those skilled in the art will understand that a direct relationship exists between the size of pores and the overall ratio of expansion or deformability of an implantable graft. Generally, therefore, it is appreciated that pore sizes must increase in order to increase the effective attainable degree of expansion or deformation of the graft.

For applications where large deformation and small pore size are both requirements, in accordance with another aspect of the inventive graft embodiment, it is contemplated that two or more graft members are employed such as diametrically concentric grafts for tubular configurations. The two or more graft members have a pattern of a plurality of microperforations passing there through, with the plurality of patterned microperforations being positioned out of phase relative to one another such as to create a tortuous cellular migration pathway through the wall of the concentrically engaged first and second graft members as well as a smaller effective pore size. In order to facilitate cellular migration through and healing of the first and second graft members in vivo, it may be preferable to provide additional cellular migration pathways that communicate between the plurality of microperforations in the first and second graft members. These additional cellular migration pathways, if necessary, may be imparted as 1) a plurality of projections formed on either the luminal surface of the second graft or the abluminal surface of the first graft, or both, which serve as spacers and act to maintain an annular opening between the first and second graft members that permits cellular migration and cellular communication between the plurality of microperforations in the first and second graft members, 2) a plurality of microgrooves, which may be random, radial, helical, or longitudinal relative to the longitudinal axis of the first and second graft members, the plurality of microgrooves being of a sufficient size to permit cellular migration and propagation along the groove, the microgrooves serve as cellular migration conduits between the plurality of microperforations in the first and second graft members, or 3) where the microperforations are designed to impart an out of plane motion of the graft material upon deformation, thereby keeping a well defined space between the planes originally defining the facing surfaces of the grafts.

The graft member or members may be formed as a monolayer film, or may be formed from a plurality of film layers formed one upon another. The particular material used to form each layer of biocompatible metal and/or pseudometal is chosen for its biocompatibility, corrosion-fatigue resistance and mechanical properties, i.e., tensile strength, yield strength. The metals include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. Additionally, each layer of material used to form the graft may be doped with another material for purposes of improving properties of the material, such as radiopacity or radioactivity, by doping with tantalum, gold, or radioactive isotopes.

DETAILED DESCRIPTION OF THE PREFERRED EMBODIMENTS

With the foregoing as background, we turn now to a description of the present invention with reference the preferred embodiments thereof and with reference to the accompanying figures. As noted above, the inventive microporous metallic implantable devices may assume a wide number of geometric configurations, including, for example, planar sheets, tubes or toroids. For ease of reference, however, the accompanying figures and the following description of the invention will refer to tubular implantable graft members. Those skilled in the art, however, will understand that this is merely an exemplary geometric configuration and is not intended to limit the scope of the invention to tubular members or be limited in application to graft members.

Figure 1:
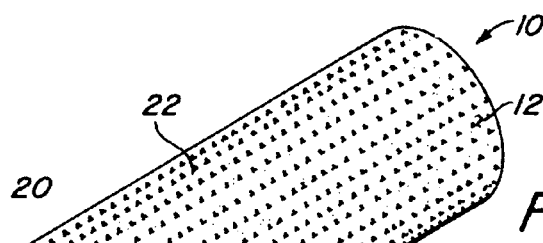
FIG. 1 is a perspective view of the inventive graft.

With particular reference to FIG. 1, the inventive implantable medical device is illustrated as a graft 10. Graft 10 consists generally of a body member 12 having a first surface 14 and a second surface 16 and a thickness 18 intermediate the first surface 14 and the second surface 16. A plurality of microperforations 20 is provided and pass through the thickness 18 of the body member 12 with interperforation regions 22 of the body member 12 between adjacent microperforation 20. The plurality of microperforations 20 each preferably have a geometric configuration that is susceptible of geometric change, such that the open surface area of each microperforation 20 may change under an externally applied load. Each of the plurality of microperforations 20 in the undeformed state preferably has an open surface area less than about 2 mm$^2$, with the total open surface area of the graft in the undeformed state being between 0.001 to 99%. The open surface area of the plurality of microperforations and the open surface area of the graft may change considerably upon deformation of the plurality of microperforations 20. Both the size of the microperforations 20 in the deformed and undeformed state and the total open area of the graft 10 in the deformed and undeformed state may be selected in view of the following non-exclusive factors based on the graft application: 1) the desired compliance of the graft 10, 2) the desired strength of the graft 10, 3) desired stiffness of the graft 10, 4) the desired degree of geometric enlargement of the microperforations 20 upon deformation and 5) in some cases, such as with vascular grafts, the desired delivery profile and post delivery profile.

In accordance with a preferred embodiment of the present invention, the plurality of microperforations 20 is patterned in such a manner as to define deformation regions of the body member 12. The thickness 18 is between 0.1 μm and 75 μm, preferably between 1 μm and 50 μm., and most preferably between about 2 μm and 25 μm. When fabricated within these thickness ranges, the graft 10 has a thickness 18 which is thinner than the wall thickness of conventional non-metallic implantable grafts and that of conventional metal endoluminal stents.

The plurality of microperforations is patterned in a regular array forming a regular array of microperforations 20 in both the longitudinal and circumferential axes of the body member 12. For purposes of reference, the pattern of microperforations 20 will, hereinafter, be described with reference to a planar X-Y axes, which in a tubular member will correspond to the longitudinal or circumferential axes of the tubular member. Those of ordinary skill in the art will understand that reference to X-axis or Y-axis when applied to a tubular member may be used such that the term "X-axis" may correspond to either the longitudinal axis or circumferential direction of the tubular member and the term "Y-axis" may refer to the corresponding circumferential direction or longitudinal axis or the tubular member.

It will be appreciated by those of ordinary skill in the art that individual different geometric patterns may have associated intended uses, function or mechanical requirements of a particular device. Thus, the particular intended use of the implantable member 10 will be a consideration in the selection of the particular geometric pattern for the plurality of microperforations 20. For example, where the implantable member 10 has an intended use as a free-standing implantable endoluminal vascular graft, a large circumferential expansion ratio and longitudinal flexibility may be desirable. Thus, a particular geometry of the plurality of microperforations 20 that offers these properties will be selected. The plurality of microperforations 20 also affect the material properties of the implantable member 10. For example, the geometry each microperforation 20 may be altered so that each microperforation 20 exhibits stress-strain relief capabilities or the microperforations 20 may control whether geometric deformation of the microperforations 20 are plastic, elastic or superelastic deformation. Thus, both the geometry of the individual microperforations 20, the orientation of the microperforations 20 relative to the X-Y axis of the implantable member 10 and the pattern of the microperforations 20 may be selected to directly impart, affect or control the mechanical and material properties of the implantable member 10.

Figure 2A:
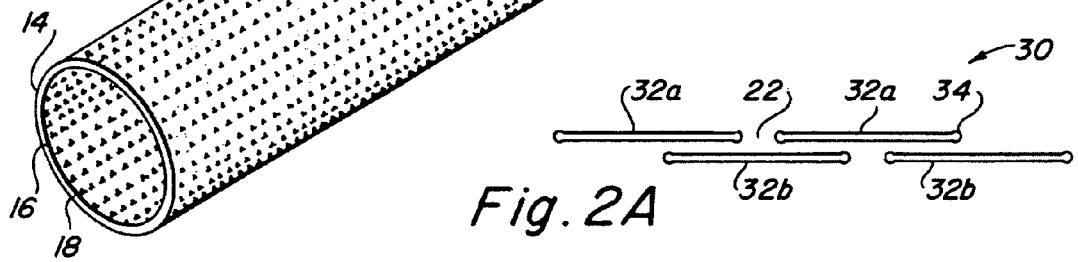
FIG. 2A is a fragmentary plan view depicting a first pattern of microperforations useful in the present invention.
Figures 2B, 2C:
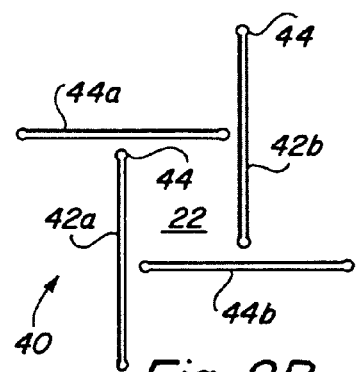
FIG. 2B is a fragmentary plan view depicting a second pattern of microperforations useful in the present invention.
FIG. 2C is a fragmentary plan view depicting a third pattern of microperforations useful in the present invention.

Different geometric patterns for the plurality of microperforations 20 in accordance with the preferred embodiments of the invention are illustrated in FIGS. 2A-2C. FIG. 2A illustrates a first geometry for each of the plurality of microperforations 20. In accordance with this first geometry, each of the plurality of microperforations 20 consist of generally elongated slots 32a, 32b. Each of the generally elongated slots 32a, 32b preferably include terminal fillets 34 on opposing ends of each elongated slot 32a, 32b. The terminal fillets 34 serve a strain relief function that aids in strain distribution through the interperforation regions 22 between adjacent slots 32. FIG. 2A further illustrates a first geometric pattern for the plurality of microperforations 32a, 32b, wherein a first row of a plurality of microperforations 32a is provided with adjacent microperforations 32a being arrayed in end-to-end fashion along a common axis, and a second row of a plurality of microperforations 32b is provided with adjacent microperforations 32b being arrayed in end-to-end fashion along a common axis with one another and with the microperforations 32a. The first row of microperforations 32a and the second row of microperforations 32b are offset or staggered from one another, with an end of a microperforation 32a being laterally adjacent to an intermediate section of a microperforation 32b, and an end of microperforation 32b being laterally adjacent an intermediate section of a microperforation 32a.

The first geometry 30 of the plurality of microperforations 32a, 32b illustrated in FIG. 2A permits a large deformation along an axis perpendicular to a longitudinal axis of the slots. Thus, where the longitudinal axis of slots 32a, 32b is co-axial with the longitudinal axis of the implantable member 10, deformation of the slots 32a, 32b will permit circumferential compliance and/or expansion of the implantable member 10. Alternatively, where the longitudinal axis of the slots 32a, 32b is parallel to the circumferential axis of the implantable member 10, the slots 32a, 32b permit longitudinal compliance, flexibility and expansion of the implantable member 10.

FIG. 2B illustrates a second geometry 40 for the plurality of microperforations 20 and consists of a plurality of microperforations 42a, 44b, again having a generally elongate slot-like configuration like those of the first geometry 30. In accordance with this second geometry 40, individual microperforations 42a and 44b are oriented orthogonal relative to one another. Specifically, a first microperforation 42a is oriented parallel to an X-axis of the implantable member 10, while a first microperforation 44b is positioned adjacent to the first microperforation 44a along the X-axis, but the first microperforation 44b is oriented perpendicular to the X-axis of the implantable member 10 and parallel to the Y-axis of the implantable member 10. Like the first geometry, each of the plurality of microperforations 42a, 44b may include a terminal fillet 44 at opposing ends of the slot of each microperforation in order to serve a strain relief function and transmit strain to the interperforation region 22 between adjacent microperforations. This second geometry 40 offers a balance in both compliance and degree of expansion in both the X and Y-axes of the implantable device 12

In each of FIGS. 2A and 2B, each of the microperforations 32a, 32b, 42a, 44b has a generally longitudinal slot configuration. Each of the generally longitudinal slots may be configured as a generally linear or curvilinear slot. In accordance with the preferred embodiments of the invention, however, it is preferred to employ generally linear slots.

FIG. 2C illustrates a third preferred geometry 50 for the plurality of microperforations. In accordance with this third geometry 50, each of the plurality of microperforations 52 has a generally trapezoidal or diamond-like shape with interperforation graft regions 56 between adjacent pairs of microperforations 52. It will be appreciated that the third geometry 50 may be achieved by geometrically deforming the first geometry 30 along an axis perpendicular to the longitudinal axis of the plurality of microperforations 32a, 32b. Similarly, the first geometry 30 may be achieved by deforming microperforations 52 in the third geometry 50 along either an X-axis or a Y-axis of the implantable member 10.

Figure 3A:
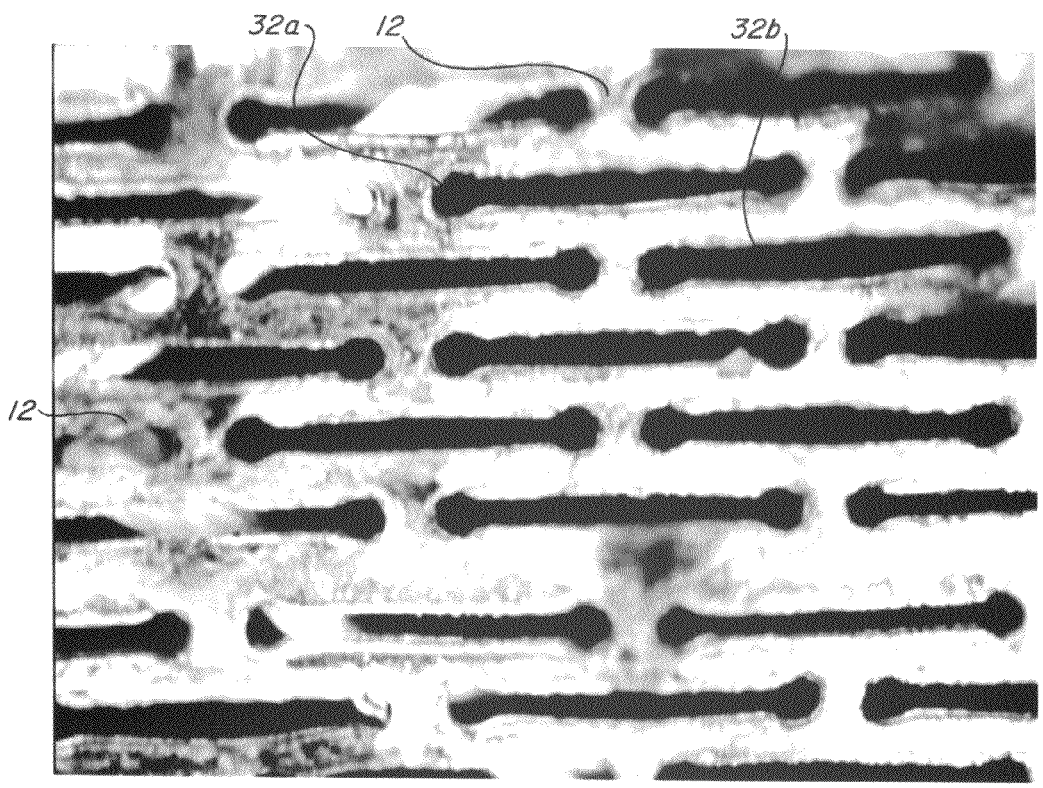
FIG. 3A is photomicrograph depicting the inventive graft having the first pattern of microperforation depicted in FIG. 2A in a geometrically undeformed state.
Figure 3B:
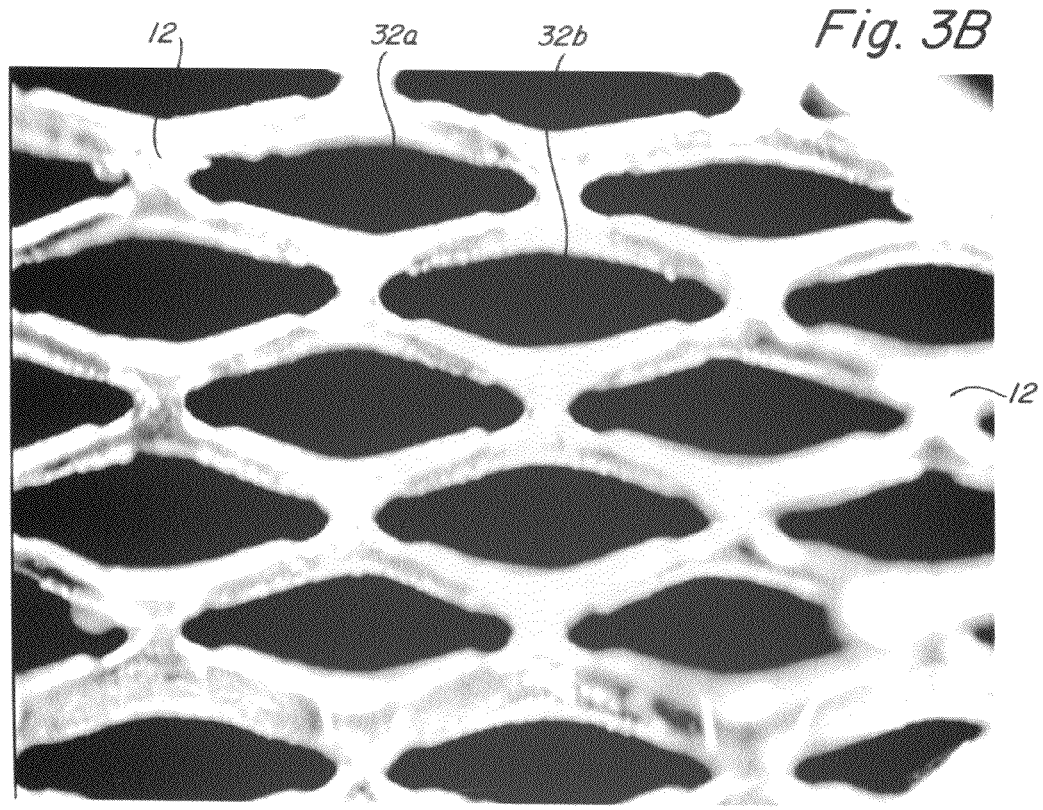
FIG. 3B is a photomicrograph of the inventive graft illustrated in FIG. 3A showing the microperforations in a geometrically deformed state.

FIGS. 3A and 3B are photomicrographs illustrating the inventive implantable device 12 having a plurality of microperforations formed as generally longitudinal slots 32a, 32b in accordance with the first geometry depicted in FIG. 2A. Each of the plurality of microperforations were formed with an orientation parallel to the longitudinal axis of the implantable device 12. The implantable device 12 consists of a 6 mm inner diameter NiTi shape memory tubular graft member having a wall thickness of 5 μm. FIG. 3A depicts the plurality of microperforations 32a and 32b in their undeformed state, while FIG. 3B depicts the plurality of microperforations 32a and 32b in their geometrically deformed state under the influence of stain applied perpendicular to the longitudinal axis of the implantable graft 12. It may be clearly understood that geometric deformation of the plurality of microperforations 32a, 32b permitted circumferential expansion of the inventive graft. The dimensions of each of the plurality of microperforations in their undeformed state depicted in FIGS. 3A and 3B was 430 μm in length, 50 μm width, with the terminal fillets having a 50 μm diameter.

Figure 4:
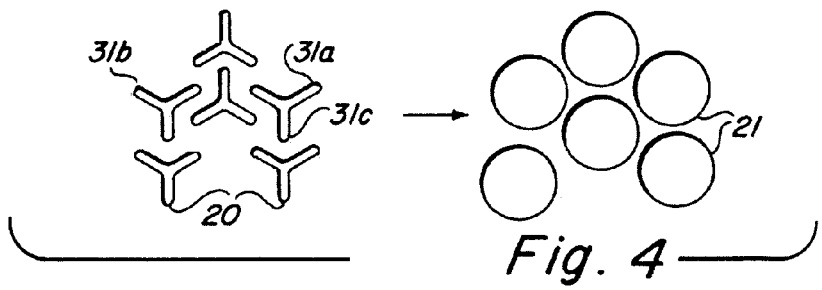
FIG. 4 is a diagrammatic illustration depicting geometric deformation of the fourth pattern of microperforations in FIG. 2D.
Figure 2D:
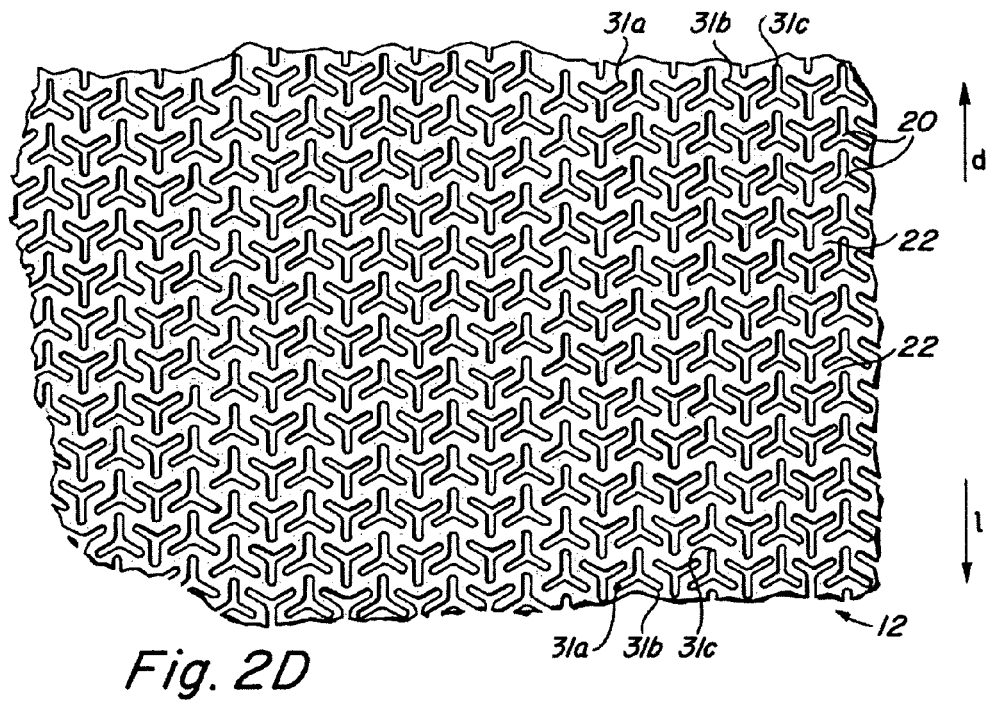
FIG. 2D is a fragmentary plan view depicting a fourth pattern of microperforations useful in the present invention.

In accordance with a fourth geometry of the plurality of microperforations 20 illustrated in FIGS. 2D and 4, each of the plurality of microperforations 20 have a generally tri-legged or Y-shaped configuration. The Y-shaped configuration of each of the plurality of microperforations 20 has three co-planar radially projecting legs 31a, 31b, 31c, each offset from the other by an angle of about 120 degrees thereby forming a generally Y-shape. Each of the three co-planar radially projecting legs 31a, 31b, 31c may be symmetrical or asymmetrical relative to one another. However, in order to achieve uniform geometric deformation across the entire graft body member 12, it is preferable that each of the plurality of microperforations 20 has geometric symmetry. Those skilled in the art will recognize that beyond the two particular patterns described here any number of different patterns may be used without significantly departing from the inventive graft concept described in the present patent.

Those skilled in the art will understand that each of the microperforations 20 are capable of undergoing deformation upon application of a sufficient force. In a tubular geometry, the graft 12 may deform both circumferentially and longitudinally. As is illustrated in FIG. 3a, each of the plurality of elongated slots may deform into opened microperforations which assume a generally rhomboidal shape. Similarly, Y-shaped microperforations 20 shown in FIG. 4 are capable of deformation into generally circular or oval open microperforations 21. The deformation regions 22 between adjacent microperforations 20 facilitate deformation of each of the plurality of microperforations 20 by deforming to accommodate opening of each of the plurality of microperforations 20.

Figure 5:
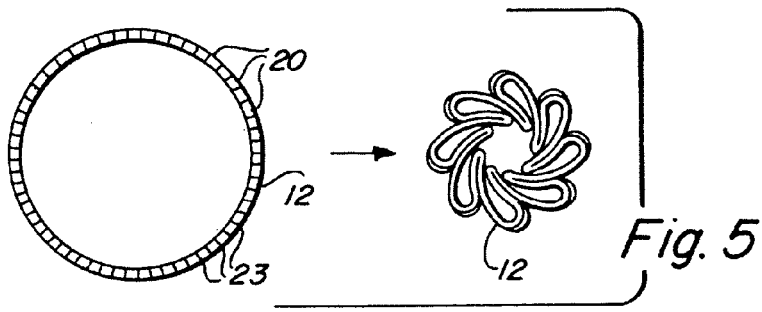
FIG. 5 is a diagrammatic cross-sectional view illustration depicting the inventive graft assuming a folded condition suitable for endoluminal delivery.

As depicted in FIG. 5, the inventive graft 12 may be folded to assume a smaller diametric profile for endoluminal delivery. In order to facilitate folding, the pattern of the plurality of microperforations 20 may be fashioned to create a plurality of folding regions 23, that constitute relatively weakened regions of the graft 12, to permit folding the graft 12 along folding regions 23.

Figure 6:
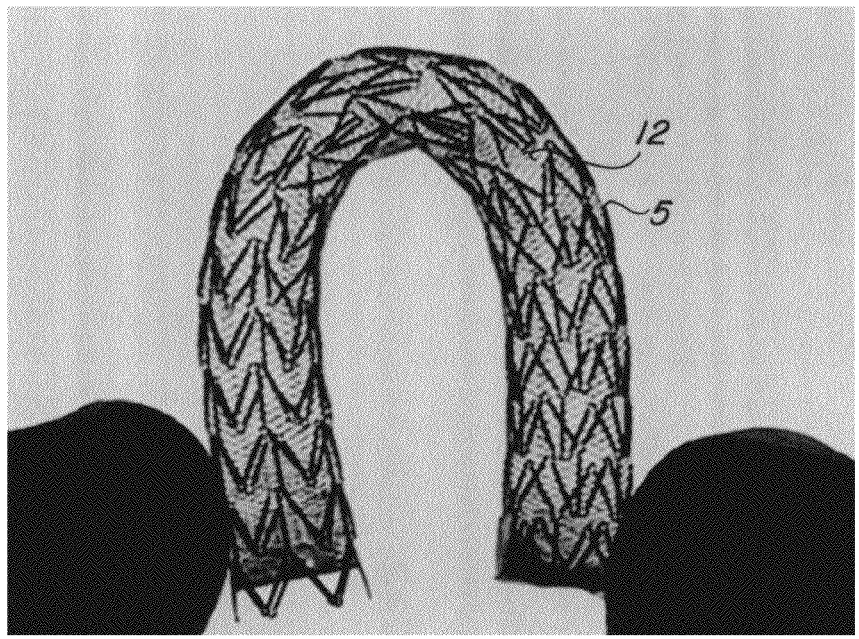
FIG. 6 is a photographic illustration of the inventive graft used as a stent covering.

FIG. 6 is a photographic illustration of the inventive microporous graft 12 circumferentially mounted onto an endoluminal stent 5. It may be readily seen that the microporous graft 12 exhibits mechanical properties of high longitudinal flexibility and both radial and circumferential compliance.

Figure 7:
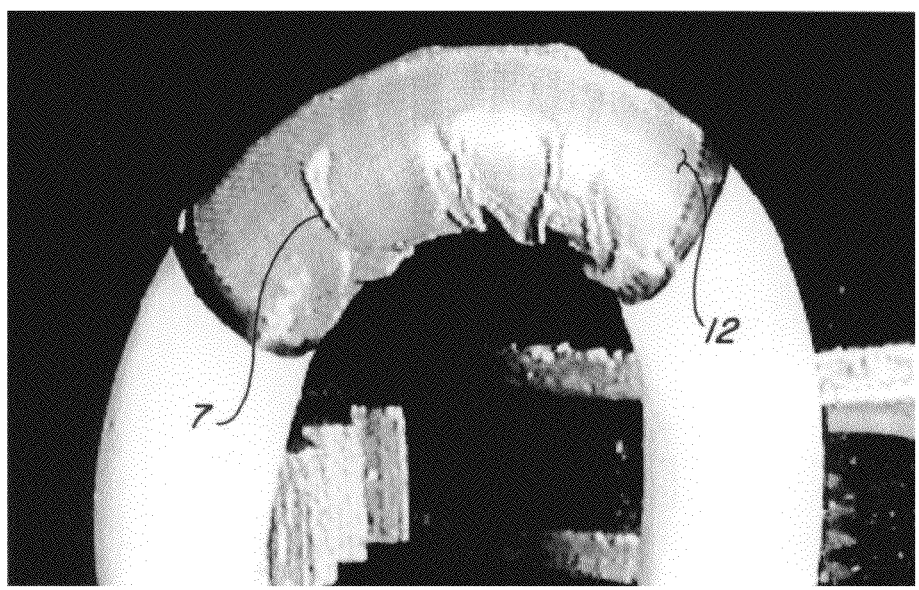
FIG. 7 is a photographic illustration of the inventive graft deformed approximately 180 degrees along its longitudinal axis illustrating the fabric-like quality of the graft.

FIG. 7 is a photographic illustration of the inventive microporous graft 12 mounted onto mandrel and flexed approximately 180 degrees along its longitudinal axis. Upon longitudinal flexion, the inventive graft 12 undergoes a high degree of folding with a plurality of circumferentially oriented folds 7, characteristic of its fabric-like qualities.

Figure 8A:
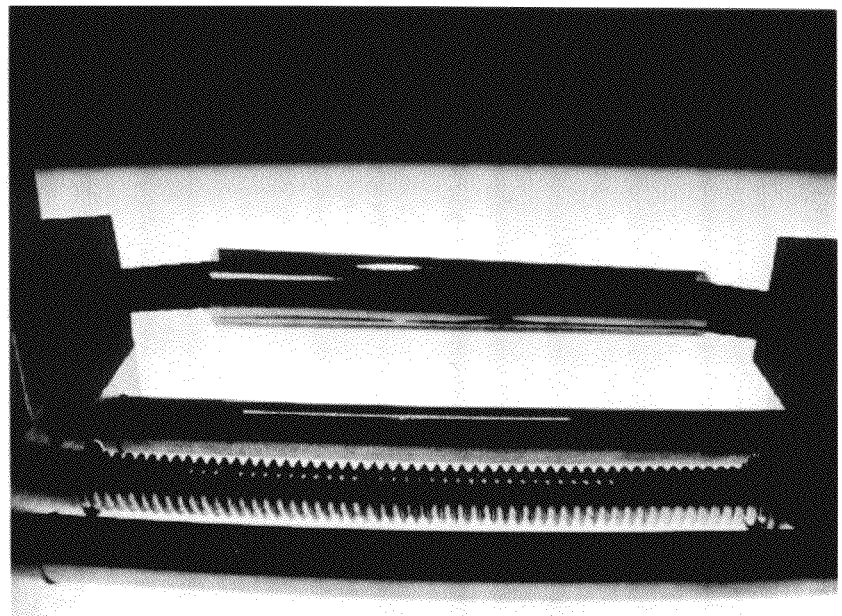
FIG. 8A is a photographic illustration of the inventive graft circumferentially covering a braided expansion member and mounted on an expansion jig that exerts a compressive force along the longitudinal axis of the braided expansion member and which radially expands the braided expansion member.
Figure 8B:
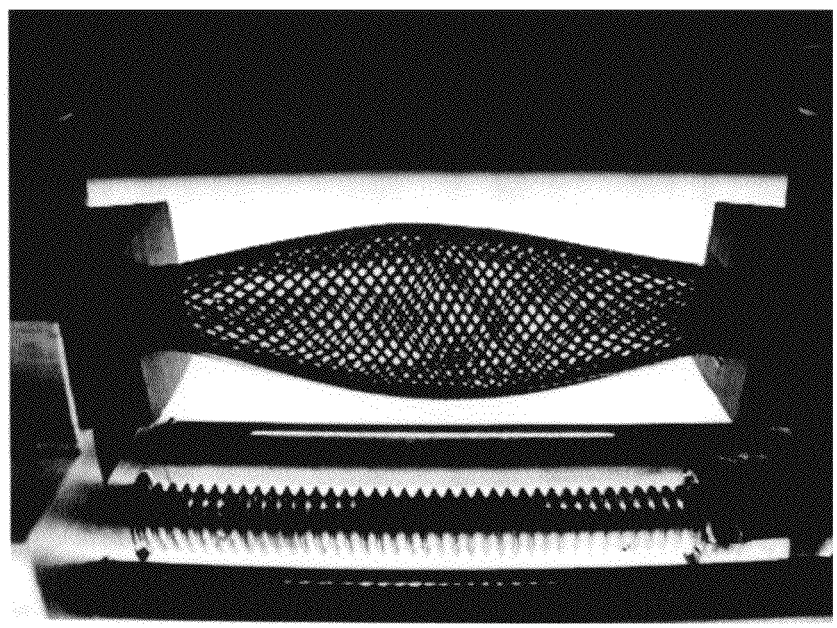
FIG. 8B is a photographic illustration of the inventive graft radially exhibiting radial compliance under the influence of a radially expansive force.

FIGS. 8A and 8B are photographic reproductions illustrating the high degree of circumferential compliance of the inventive microporous graft 12. A 6 mm microporous graft having a 5 μm wall thickness was mounted concentrically over a braided pseudostent. An axial force was applied along the longitudinal axis of the braided pseudostent causing the pseudostent to radially expand and exert a circumferentially expansive force to the inventive graft 12. As is clearly depicted in FIGS. 8A and 8B the plurality of micropores in the inventive graft 12 geometrically deform thereby permitting circumferential expansion of the graft 12.

Thus, one embodiment of the present invention provides a new metallic and/or pseudometallic implantable graft that is biocompatible, geometrically changeable either by folding and unfolding or by application of a plastically, elastically or superelastically deforming force, and capable of endoluminal delivery with a suitably small delivery profile. Suitable metal materials to fabricate the inventive graft are chosen for their biocompatibility, mechanical properties, i.e., tensile strength, yield strength, and their ease of fabrication. The compliant nature of the inventive graft material may be employed to form the graft into complex shapes by deforming the inventive graft over a mandrel or fixture of the appropriate design. Plastic deformation and shape setting heat treatments may be employed to ensure the inventive implantable members 10 retain a desired conformation.

Figure 9:
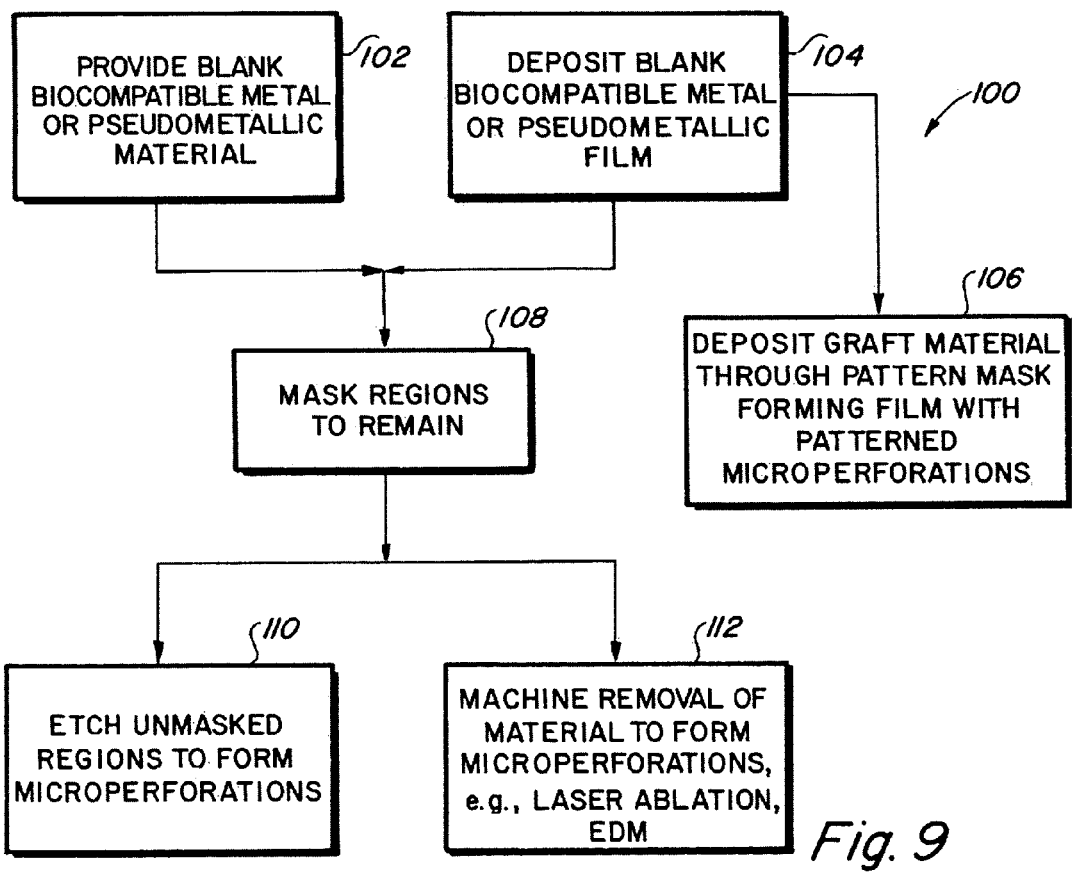
FIG. 9 is a flow diagram depicting alternate embodiments of making the inventive graft.

According to a first preferred method of making the graft of the present invention, the graft is fabricated of vacuum deposited metallic and/or pseudometallic films. With particular reference to FIG. 9, the fabrication method 100 of the present invention is illustrated. A precursor blank of a conventionally fabricated biocompatible metal or pseudometallic material may be employed at step 102. Alternatively, a precursor blank of a vacuum deposited metal or pseudometallic film may be employed at step 104. The precursor blank material obtained either from step 102 or step 104 is then preferably masked at step 108 leaving exposed only those regions defining the plurality of microperforations. The exposed regions from step 108 are then subjected to removal either by etching at step 110, such as by wet or dry chemical etching processing, with the etchant being selected based upon the material of the precursor blank, or by machining at step 112, such as by laser ablation or EDM. Alternatively, when employing the vacuum deposition step 104, a pattern mask corresponding to the plurality of microperforations may be interposed at step 106 between the target and the source and the metal or pseudometal deposited through the pattern mask to form the patterned microperforations. Further, when employing the vacuum deposition step 104, plural film layers maybe deposited to form a multilayer film structure of the film prior to or concurrently with forming the plurality of microperforations.

Thus, the present invention provides a new metallic and/or pseudometallic implantable graft that is biocompatible, compliant, geometrically changeable either by folding and unfolding or by application of a plastically, elastically or superelastically deforming force, and, in some cases, capable of endoluminal delivery with a suitably small delivery profile and suitably low post-delivery profile. Suitable metal materials to fabricate the inventive graft are chosen for their biocompatibility, mechanical properties, i.e., tensile strength, yield strength, and in the case where vapor deposition is deployed, their ease of deposition include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. Examples of pseudometallic materials potentially useful with the present invention include, for example, composite materials and ceramics.

The present invention also provides a method of making the inventive expandable metallic graft by vacuum deposition of a graft-forming metal or pseudometal and formation of the microperforations either by removing sections of deposited material, such as by etching, EDM, ablation, or other similar methods, or by interposing a pattern mask, corresponding to the microperforations, between the target and the source during deposition processing. Alternatively, a pre-existing metal and/or pseudometallic film manufactured by conventional non-vacuum deposition methodologies, such as wrought hypotube or sheet, may be obtained, and the microperforations formed in the pre-existing metal and/or pseudometallic film by removing sections of the film, such as by etching, EDM, ablation, or other similar methods. An advantage of employing multilayer film structures to form the inventive graft is that differential functionalities may be imparted in the discrete layers. For example, a radiopaque material such as tantalum may form one layer of a structure while other layers are chosen to provide the graft with its desired mechanical and structural properties.

In accordance with the preferred embodiment of fabricating the inventive microporous metallic implantable device in which the device is fabricated from vacuum deposited nitinol tube, a cylindrical deoxygenated copper substrate is provided. The substrate is mechanically and/or electropolished to provide a substantially uniform surface topography for accommodating metal deposition thereupon. A cylindrical hollow cathode magnetron sputtering deposition device was employed, in which the cathode was on the outside and the substrate was positioned along the longitudinal axis of the cathode. A cylindrical target consisting either of a nickel-titanium alloy having an atomic ratio of nickel to titanium of about 50-50% and which can be adjusted by spot welding nickel or titanium wires to the target, or a nickel cylinder having a plurality of titanium strips spot welded to the inner surface of the nickel cylinder, or a titanium cylinder having a plurality of nickel strips spot welded to the inner surface of the titanium cylinder is provided. It is known in the sputter deposition arts to cool a target within the deposition chamber by maintaining a thermal contact between the target and a cooling jacket within the cathode. In accordance with the present invention, it has been found useful to reduce the thermal cooling by thermally insulating the target from the cooling jacket within the cathode while still providing electrical contact to it. By insulating the target from the cooling jacket, the target is allowed to become hot within the reaction chamber. Two methods of thermally isolating the cylindrical target from the cooling jacket of the cathode were employed. First, a plurality of wires having a diameter of 0.0381 mm were spot welded around the outer circumference of the target to provide an equivalent spacing between the target and the cathode cooling jacket. Second, a tubular ceramic insulating sleeve was interposed between the outer circumference of the target and the cathode cooling jacket. Further, because the Ni—Ti sputtering yields can be dependant on target temperature, methods which allow the target to become uniformly hot are preferred.

The deposition chamber was evacuated to a pressure less than or about $2-5\times 10^{-7}$ Torr and pre-cleaning of the substrate is conducted under vacuum. During the deposition, substrate temperature is preferably maintained within the range of 300 and 700 degrees Centigrade. It is preferable to apply a negative bias voltage between 0 and $-1000$ volts to the substrate, and preferably between $-50$ and $-150$ volts, which is sufficient to cause energetic species arriving at the surface of the substrate. During deposition, the gas pressure is maintained between 0.1 and 40 mTorr but preferably between 1 and 20 mTorr. Sputtering preferably occurs in the presence of an Argon atmosphere. The argon gas must be of high purity and special pumps may be employed to reduce oxygen partial pressure. Deposition times will vary depending upon the desired thickness of the deposited tubular film. After deposition, the plurality of microperforations are formed in the tube by removing regions of the deposited film by etching, such as chemical etching, ablation, such as by excimer laser or by electric discharge machining (EDM), or the like. After the plurality of microperforations are formed, the formed microporous film is removed from the copper substrate by exposing the substrate and film to a nitric acid bath for a period of time sufficient to remove dissolve the copper substrate.

EXAMPLE

Figure 10A:
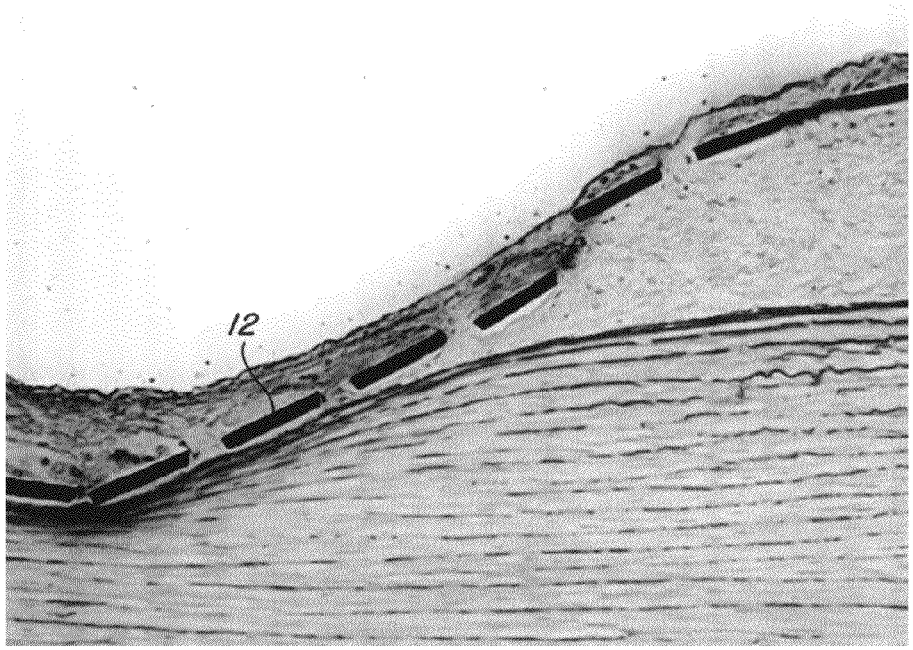
FIG. 10A is a histology slide, stained with hematoxylin and eosin, from a 28 day explanted swine carotid artery having the inventive graft implanted therein.
Figure 10B:
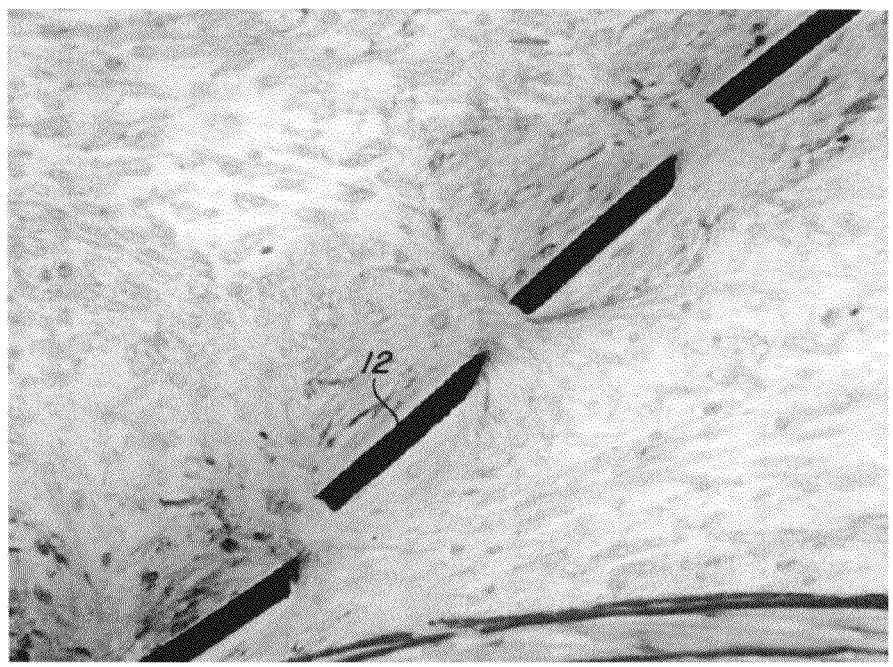
FIG. 10B is a histology slide, stained with hematoxylin and eosin, from a 28 day explanted swine carotid artery having the inventive graft implanted therein.

A 5 μm thick NiTi graft having a pattern of microperforations consisting of parallel staggered longitudinally oriented linear slots, each slot being 430 μm length, 25 μm width, and having 50 μm diameter fillets on each end of each linear slot, was mounted onto a 6 mm NiTi stent and delivered endoluminally to the left carotid artery of a swine. After 28 days, the swine was euthanized, and the graft explanted from the left carotid artery. Samples were prepared using standard hematoxylin and eosin staining procedures, and microscope slides prepared. As illustrated in FIGS. 10A histology of the explanted samples revealed complete endothelialization around the graft 12, negligible neointimal proliferation with the absence of trauma to the internal elastic lamina. FIG. 10B is a sample indicating cross-talk between the arterial superficial and deep layers with the transmural formation of small capillaries.

Figure 11:
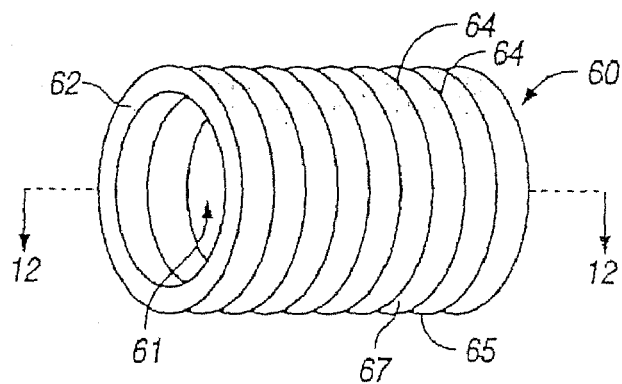
FIG. 11 is a perspective view of an alternative embodiment of the inventive graft.
Figure 12:
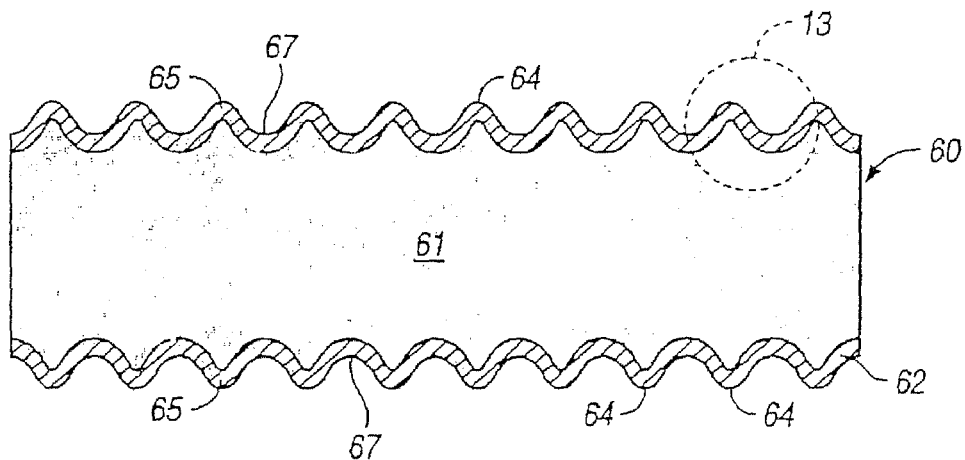
FIG. 12 is a cross-sectional view taken along line 12-12 of FIG. 11.
Figure 13:
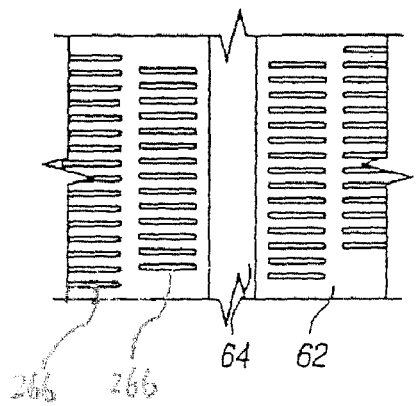
FIG. 13 is an magnified view of region 13 of FIG. 12.
Figure 14:
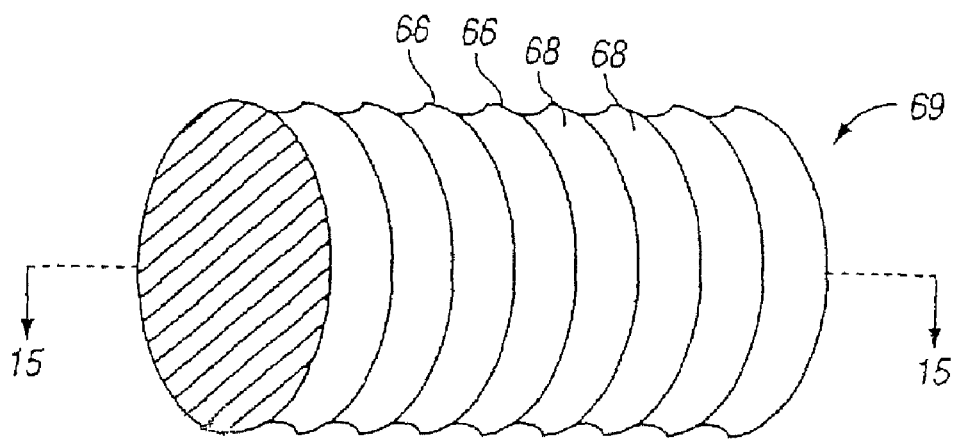
FIG. 14 is a perspective view of a forming mandrel for making the alternative embodiment of the inventive graft.
Figure 15:
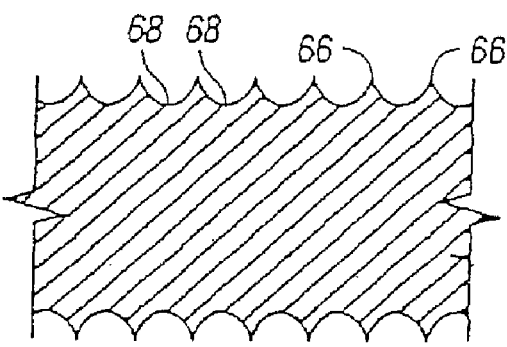
FIG. 15 is a cross-sectional view taken along line 15-15 of FIG. 14.

Alternate embodiments of the inventive graft are depicted in FIGS. 11-13 and FIGS. 16-17, and a forming substrate for making the alternate embodiments is depicted in FIGS. 14-15. With particular reference to FIGS. 11-13, a graft 60 having a generally tubular configuration with a central longitudinal lumen 61 is depicted. Graft 60 consists generally of a graft body member 62 that is preferably formed entirely of at least one vacuum deposited metallic or pseudometallic material as described above with reference to the previously described inventive graft materials. The graft body member 62 has first and second wall surfaces forming lumenal and ablumenal surfaces of the graft body member and a plurality of corrugations or pleats 64 forming an undulating pattern of peaks 65 and valleys 67 in wall surfaces of the graft body member 62.

As illustrated in FIG. 13, the graft 60 preferably has a plurality of microperforations 266 passing through the wall surfaces of the graft body member 62 and communicating between the ablumenal and lumenal wall surfaces of the graft 60. Like the previously described embodiments of the inventive graft, the plurality of microperforations 266 in the inventive graft 60 may be formed of a wide variety of geometries and dimensions so as impart geometric compliance to the graft, geometric distendability to the graft and/or limit or permit the passage of body fluids or biological matter through the graft, such as facilitating transmural endothelialization while preventing fluid flow through the wall of the graft under normal physiological conditions. The plurality of microperforations may also impart a fabric-like quality to the graft by imparting pliability and/or elastic, plastic or superelastic compliance to the graft, such as that required for longitudinal flexibility in the case of a vascular graft.

The plurality of microperforations 266 may be present along the entire longitudinal length of the graft body member 62 and about the entire circumferential axis of the graft member 62. Alternatively, the plurality of microperforations 266 may be present only in selected regions along either the longitudinal length or the circumferential axis of the graft body member 62. The positioning of the plurality of microperforations 266 may be selected based upon various criteria, including, without limitation, the indication of use of the graft, the anatomical placement of the graft, and whether the graft is surgically implanted and requires sutures or whether it is used endoluminally without sutures.

Figure 16:
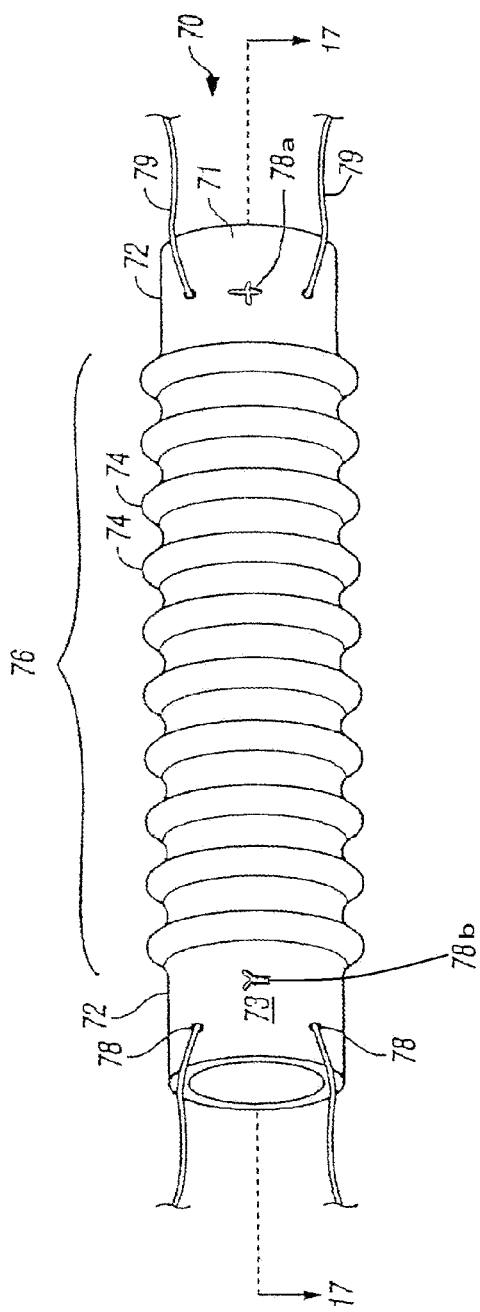
FIG. 16 is a perspective view of a second alternative embodiment of the inventive graft.
Figure 17:
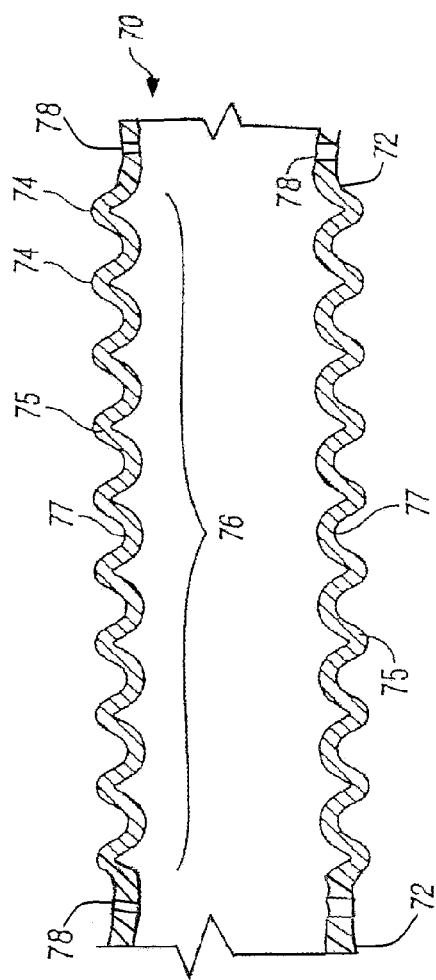
FIG. 17 is a perspective view taken along line 17-17 of FIG. 16.

Turning to FIGS. 16-17 there is depicted a second alternative embodiment of the inventive graft 70. Like graft 60 depicted in FIGS. 11-13, graft 70 consists of a generally tubular graft body member 72 having first and second wall surfaces forming lumenal and ablumenal surfaces of the tubular graft body member 72, and a plurality of circumferential corrugations or pleats 74 forming an undulating pattern of peaks 75 and valleys 77 in the wall surfaces of the tubular graft body member 72. The plurality of corrugations or pleats 74 are preferably positioned along an intermediate region 76 of the graft 70, with opposing end regions 71, 73, that form proximal and distal ends of the graft 70, having no corrugations or pleats 74. Alternatively, the proximal and distal ends of the graft 70 may have longitudinal regions with circumferential corrugations or pleats 74 and other longitudinal regions without circumferential corrugations or pleats 74, thereby having staggered arrays of corrugated and non-corrugated regions at the opposing ends 71, 73 of the graft 70.

In one aspect of the inventive graft 70 the opposing end regions 71, 73 of the graft body member 72 may have a z-axis thickness that is either greater than or less than the z-axis thickness of the intermediate region 76. Additionally, a plurality of suture apertures 78 are provided and preferably pass through the opposing ends 71, 73 of the graft 70 and permit sutures 79 to pass through the suture apertures 78 for purposes of affixing the graft 70 to anatomical structures in vivo. In one embodiment of the invention, the suture apertures/openings may have a generally cruciform-shaped slot pattern 78a or a generally Y-shaped slot pattern 7b.

Like each of the foregoing embodiments, the grafts 60 and 70 are preferably fabricated entirely of biocompatible metal and/or pseudometallic materials. By fashioning the inventive grafts 60, 70 entirely of biocompatible metal and/or pseudometallic materials, the grafts 60, 70 exhibit a greater capacity for endothelialization without the need for pre-clotting as is the case with polyethylene or DACRON grafts, and provide highly hospitable surface for re-endothelialization similar to many metal stents.

It will be understood by those skilled in the art that providing the circumferential corrugations or pleats 64, 74 in grafts 60, 70 imparts a large degree of longitudinal flexibility to the grafts 60, 70 and permits the grafts to bend in excess of 180 degrees about its longitudinal axis. This large degree of longitudinal flexibility in an all metal or pseudometallic graft permits the graft to traverse highly tortuous delivery pathways when used as either an endoluminal graft or as a surgically-implanted graft, and be highly compliant and flexible after implantation to accommodate normal flexion and extension during ambulatory motion of the patient.

As noted above, the preferred method for fabricating the inventive grafts 60, 70 is by physical vapor deposition of a metal or pseudometallic material onto a sacrificial substrate or mandrel. A suitable sacrificial substrate or mandrel for fabricating the inventive grafts 60, 70 is illustrated in FIGS. 14-15. A generally cylindrical substrate 69 is provided for vacuum deposition. The generally cylindrical substrate may be either a solid or a tubular blank of a metal material 66 that is susceptible to differential degradation relative to the metal graft deposited thereupon during vacuum deposition. In order to form the inventive grafts 60, 70, the generally cylindrical substrate 69 is formed with a plurality of circumferential undulations defining a plurality of peaks 66 and valleys 68. The plurality of peaks 66 and valleys 68 in the cylindrical substrate 69 are positioned to correspond to the position of the peaks and valleys formed in the conformal deposited layer that forms the grafts 60, 70. The remaining process parameters describe above may be followed to form the plurality of micro perforations in the grafts 60, 70.

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto.

What is claimed is:

1. An implantable medical graft, comprising:
   a. a generally tubular body member comprising a film selected from the group consisting of metallic and pseudometallic materials and having a luminal wall surface, an abluminal wall surface and a wall thickness intermediate the luminal wall surface and the abluminal wall surface;
   b. at least a portion of the body member having a plurality of circumferential corrugations defined by a radially undulating pattern of longitudinally alternating radially extending peaks and valleys in the abluminal wall surface of the body member and a radially undulating longitudinally alternating pattern of radially extending peaks and valleys in the luminal wall surface of the body member, wherein each peak in the luminal surface is longitudinally coincident with each peak in the abluminal surface and each valley in the luminal surface is longitudinally coincident with each valley in the abluminal surface, wherein a plurality of microperforations is disposed through the wall thicknesses composing the coincident peaks and the wall thicknesses composing the coincident valleys and wherein a plurality of microperforations provide fluid migration between the luminal and abluminal wall surfaces; and
   c. at least one of a plurality of non-undulating circumferential regions positioned at end regions of the body member.

2. The implantable medical graft according to claim 1, wherein at least one of a plurality of suturing openings is disposed through the wall thickness of the at least one of the plurality of non-undulating regions of the body member.

3. The implantable medical graft according to claim 1, wherein the wall thickness of the circumferential corrugations is less than the wall thickness of the non-undulating regions.

4. The implantable medical graft according to claim 3, wherein the thickness of the circumferential corrugations is between about 3-7 μm and the wall thickness of the non-undulating regions is between about 10-20 μm.

5. The implantable medical graft according to claim 2, wherein the at least one of a plurality of suturing openings further comprises a generally cruciform-shaped slot pattern.

6. The implantable medical graft according to claim 1, further comprising at least one of a plurality of suture members integrally extending along a longitudinal axis of the body member.

7. The implantable medical graft according to claim 2, wherein the at least one of a plurality of suturing openings further comprises a generally Y-shaped slot pattern.

8. The implantable medical graft according to claim 1, wherein the film is made of a metallic material selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof.

9. The implantable medical graft according to claim 1, wherein the at least one of a plurality of microperforations further comprises a generally Y-shaped slot pattern.

10. The implantable medical graft according to claim 1, further comprising at least one of a plurality of radially projecting barb members.

11. The implantable medical graft according to claim 1 wherein the circumferential corrugations forming an undulating pattern of peaks and valleys form annular ridges in the body member to permit the implantable medical graft to bend in excess of 180 degrees about the longitudinal axis of the implantable medical graft.

12. The implantable medical graft according to claim 1, wherein the at least one of a plurality of microperforations further comprises a generally elongated slot including terminal fillets on opposing ends of the slot.

13. A method of making an implantable medical graft comprising the steps of:
   a. providing a generally cylindrical substrate having a plurality of circumferentially extending continuous undulations defined by a radially undulating pattern of surfaces disposed between longitudinally alternating radially extending peaks and valleys, patterned along at least a portion of a longitudinal axis of the generally cylindrical substrate and at least one of a plurality of non-undulated circumferential regions positioned at the end regions of the substrate;
   b. vacuum depositing a graft-forming material onto the generally cylindrical substrate;
   c. releasing the deposited graft-forming material from the substrate to form a implantable medical graft including circumferential corrugations defined by a radially undulating pattern of longitudinally alternating radially extending peaks and valleys in an abluminal wall surface of the deposited graft-forming material and a radially undulating longitudinally alternating pattern of radially extending peaks and valleys in a luminal wall surface of the deposited graft-forming material, wherein each peak in the luminal surface is longitudinally coincident with each peak in the abluminal surface and each valley in the luminal surface is longitudinally coincident with each valley in the abluminal surface, wherein the peaks and valleys are disposed along at least a portion of the longitudinal axis of the deposited graft-forming material and at least one of a plurality of non-undulated circumferential regions is positioned at the end regions of the deposited graft-forming material; and
   d. forming a plurality of microperforations wherein a plurality of microperforations provide fluid migration between the luminal and abluminal wall surfaces disposed through the deposited graft-forming material forming the coincident peaks and the coincident valleys.

14. The method according to claim 13, wherein the graft-forming material is selected from the group consisting of biocompatible metals and pseudometals.

15. The method according to claim 13, further comprising the step of forming at least one of a plurality of suturing openings through the wall thickness of at least one non-undulating region of the deposited graft-forming material.

* * * * *